United States Patent
Fuji et al.

(10) Patent No.: US 10,085,445 B2
(45) Date of Patent: Oct. 2, 2018

(54) BIOCORROSION INHIBITOR FOR METAL

(71) Applicant: KURARAY CO., LTD., Kurashiki-shi (JP)

(72) Inventors: Junichi Fuji, Chiyoda-ku (JP); Yutaka Suzuki, Kamisu (JP); Kosuke Senda, Kamisu (JP); Satoshi Wakai, Kobe (JP)

(73) Assignee: KURARAY CO., LTD., Kurashiki-shi (JP)

( * ) Notice: Subject to any disclaimer, the term of this patent is extended or adjusted under 35 U.S.C. 154(b) by 48 days.

(21) Appl. No.: 15/036,477

(22) PCT Filed: Nov. 14, 2014

(86) PCT No.: PCT/JP2014/080183
§ 371 (c)(1),
(2) Date: May 13, 2016

(87) PCT Pub. No.: WO2015/072541
PCT Pub. Date: May 21, 2015

(65) Prior Publication Data
US 2016/0286799 A1    Oct. 6, 2016

(30) Foreign Application Priority Data
Nov. 15, 2013 (JP) .................................. 2013-237166

(51) Int. Cl.
| | | |
|---|---|---|
| *A01N 35/02* | (2006.01) | |
| *C23F 11/12* | (2006.01) | |
| *A61L 2/16* | (2006.01) | |
| *C07C 47/12* | (2006.01) | |

(52) U.S. Cl.
CPC ................ *A01N 35/02* (2013.01); *A61L 2/16* (2013.01); *C07C 47/12* (2013.01); *C23F 11/122* (2013.01)

(58) Field of Classification Search
CPC ............ C07C 47/12; A01N 35/02; A61L 2/16
See application file for complete search history.

(56) References Cited

U.S. PATENT DOCUMENTS 4,420,640 A * 12/1983 Matsumoto ............. C07C 45/49
502/162
2017/0081597 A1    3/2017 Fuji et al.

FOREIGN PATENT DOCUMENTS

| GB | 2 204 864 A | 11/1988 |
|---|---|---|
| JP | 61-112001 A | 5/1986 |
| JP | 63-290284 A | 11/1988 |
| JP | 4-335097 A | 11/1992 |
| WO | WO 2015/141535 A1 | 9/2015 |

OTHER PUBLICATIONS

International Search Report dated Feb. 10, 2015 in PCT/JP14/80183 Filed Nov. 14, 2014.
Extended European Search Report dated Apr. 28, 2017 in Patent Application No. 14862106.3.
P. S. Guiamet, et al., "Laboratory Studies of Biocorrosion Control Using Traditional and Environmentally Friendly Biocides: An Overview", Latin American Applied Research, XP55365918, Jan. 1, 2005, http://www.sclelo.org.ar/pdf/laar/v35n4/v35n4aD6.pdf,pp. 295-300.

* cited by examiner

*Primary Examiner* — Pancham Bakshi
(74) *Attorney, Agent, or Firm* — Oblon, McClelland, Maier & Neustadt, L.L.P.

(57) ABSTRACT

The present invention aims to provide an agent for inhibiting biocorrosion of a metal, which shows high environmental and occupational safety.
An agent for inhibiting biocorrosion of a metal, comprising 1,9-nonanedial and/or 2-methyl-1,8-octanedial as an active ingredient.

4 Claims, 1 Drawing Sheet

BIOCORROSION INHIBITOR FOR METAL

TECHNICAL FIELD

The present invention relates to an agent for inhibiting biocorrosion of a metal.

BACKGROUND ART

Biocorrosion refers to a corrosion phenomenon directly or indirectly induced by the action of microorganisms present in the environment, and many study cases have been reported (e.g., non-patent document 1 etc.). However, the mechanism of development and the like are yet to be elucidated. In recent studies, it has been reported that, when two or more kinds of microorganisms (e.g., sulfate-reducing bacterium and methane-producing bacterium etc.) are involved in biocorrosion, the actions of these microorganisms synergistically promote corrosion in some cases.

In recent years, disruption of bed-rock by high-pressure water and the like have been performed in mining fossil fuels (e.g., petroleum, natural gas, shale oil, shale gas etc.). Biocorrosion is developed on an iron pipe etc. to be a flow path of such high-pressure water, and similar biocorrosion is also observed in metal working fluids. To inhibit the biocorrosion, glutaraldehyde is frequently used.

DOCUMENT LIST

Non-Patent Document non-patent document 1: Journal of Bioscience and Bioengineering VOL. 110, No. 4, pp. 426-430 (2010)

SUMMARY OF THE INVENTION

Problems to be Solved by the Invention

Generally, frequently-used antibacterial agents often contain a highly toxic compound and, for example, a compound having the property capable of changing genetic information, namely, mutagenicity, is sometimes employed as a frequently-used antibacterial agent. Such compounds are feared to develop tumor, hereditary diseases and the like in the human body, or change ecosystem in the environmental organisms. Glutaraldehyde, which is frequently used as a biocorrosion inhibitor in fossil fuel mining, is known to have mutagenicity, and feared to influence human body and the environment. It has also been reported that glutaraldehyde has a problem in preservation stability.

It is therefore an object of the present invention to provide an agent for inhibiting biocorrosion of a metal, which shows high environmental and occupational safety as compared to glutaraldehyde, and further, high stability.

Means of Solving the Problems

According to the present invention, the above-mentioned object can be achieved by providing

[1] an agent for inhibiting biocorrosion of a metal, comprising 1,9-nonanedial and/or 2-methyl-1,8-octanedial as an active ingredient (hereinafter to be also simply referred to as "agent of the present invention");

[2] the agent of [1], wherein the aforementioned biocorrosion is caused by at least one kind selected from sulfate-reducing bacterium, nitrate-reducing bacterium, methane-producing bacterium, iodide-oxidizing bacterium, iron-oxidizing bacterium and sulfur-oxidizing bacterium;

[3] the agent of [1] or [2], which is in the form of an aqueous solution having a total concentration of the active ingredient of 1-3000 ppm; and

[4] the agent of any of [1]-[3], wherein the aforementioned metal is iron;

[5] a method of inhibiting biocorrosion of a metal, comprising placing the agent of any of [1]-[4] in an environment where a microorganism causing the biocorrosion is present;

[6] a method of inhibiting biocorrosion of a metal, comprising sterilizing the microorganism causing the biocorrosion with the agent of any of [1]-[4];

[7] use of 1,9-nonanedial and/or 2-methyl-1,8-octanedial for the inhibition of biocorrosion of a metal;

[8] use of 1,9-nonanedial and/or 2-methyl-1,8-octanedial for the production of an agent for inhibiting biocorrosion of a metal.

Effect of the Invention

Since the agent of the present invention contains 1,9-nonanedial and/or 2-methyl-1,8-octanedial as an active ingredient, it is superior in a metal biocorrosion inhibitive ability, and shows high environmental and occupational safety. The active ingredient of the agent of the present invention is also superior in the preservation stability.

DESCRIPTION OF EMBODIMENTS

Figure 1:
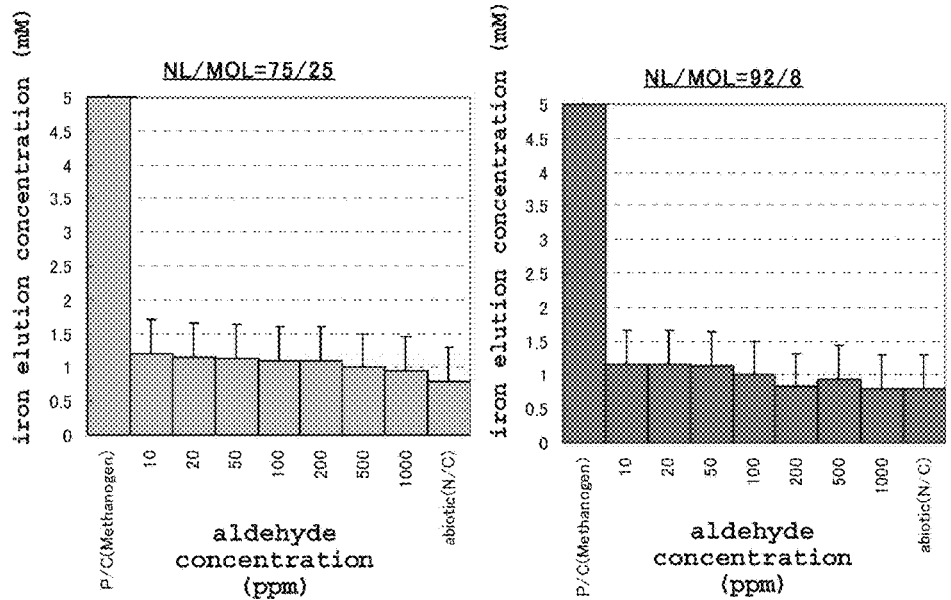
FIG. 1 shows graphs of the measurement results of iron elution concentration in a vial added with a mixture of 1,9-nonanedial and 2-methyl-1,8-octanedial in Example 1. The abbreviations in the Figure mean the following.
NL: 1,9-nonanedial
MOL: 2-methyl-1,8-octanedial
abiotic (N/C): without addition of KA-1 strain and aldehydes
P/C (Methanogen): KA-1 strain is added but aldehydes are not added

The agent of the present invention characteristically uses 1,9-nonanedial and/or 2-methyl-1,8-octanedial as an active ingredient.

The agent of the present invention contains at least one of 1,9-nonanedial and 2-methyl-1,8-octanedial as an active ingredient. As the active ingredient, 1,9-nonanedial alone or 2-methyl-1,8-octanedial alone may be used. From the aspect of industrial availability, a mixture of 1,9-nonanedial and 2-methyl-1,8-octanedial is preferable. When the agent of the present invention contains a mixture of 1,9-nonanedial and 2-methyl-1,8-octanedial as an active ingredient, the mixing ratio is not particularly limited. However, it is generally preferably 99/1-1/99, more preferably 95/5-5/95, further preferably 90/10-45/55, particularly preferably 90/10-55/45, in a mass ratio of 1,9-nonanedial/2-methyl-1,8-octanedial.

Both 1,9-nonanedial and 2-methyl-1,8-octanedial are known substances, and can be produced by a method known per se (e.g., the methods described in JP-B-2857055, JP-B-62-61577 and the like) or a method analogous thereto. In addition, commercially available products may also be used.

As long as the object of the present invention is not impaired, the agent of the present invention may further contain, besides 1,9-nonanedial and/or 2-methyl-1,8-octanedial, components conventionally used in the field of biocorrosion inhibitors. Examples of the component include other antibacterial agents, dispersing agents, suspensions, spreading agents, penetrating agents, wetting agents, mucilages, stabilizers, flame-retardants, colorants, antioxidants, antistatic agents, bubbling agents, lubricants, gellants, membrane-forming aids, antifreezing agents, viscosity modifiers, pH adjusters, preservatives, emulsifiers, antifoaming agents, carriers and the like.

Examples of other antibacterial agent include oxidants (peracetic acid, potassium peroxymonosulfate, sodium perborate, hydrogen peroxide, sodium percarbonate and the like), phosphonium salts (THPS, polyether polyamine methylene phosphonate, tributyltetradecylphosphonium chloride and the like), alkyl benzene sulfonic acids, quaternary ammonium salts (N-alkyl dimethyl benzyl ammonium chloride, N-dialkyl methyl benzyl ammonium, chloride and the like), isothiazoline-thiazoline-isothiazolone compounds (2-(thiocyanomethylthio)benzothiazole, isothiazolone and the like), thiocarbamate compounds, hydroquinone compounds, aldehyde compounds (chloroacetaldehyde and the like) other than 1,9-nonanedial and 2-methyl-1,8-octanedial, azo compounds, benzalkonium chloride, hypochlorous acid, oxazolidine compounds, imidazole compounds (1,2-dimethyl-5-nitro-IH-imidazole and the like), aminoalcohol, ethers, liposomes, alkyne alkoxylates, bromine biocide (2,2-dibromo-2-nitroacetamide and the like), enzymes (endo-β-1,2-lactanase and the like), metal ions, phenol compounds and the like. These antibacterial agents may be used alone or two or more kinds may be used in combination.

Examples of the dispersing agent include surfactants such as higher alcohol sulfate ester, alkyl sulfonic acid, alkylaryl sulfonic acid, oxyalkylamine, fatty acid ester, polyalkylene oxide, anhydrosorbitol and the like; soaps, casein, gelatin, starch, alginic acid, agar, carboxymethyl cellulose (CMC), polyvinyl alcohol, pine oil, sugar oil, bentonite, cresol soap and the like. These dispersing agents may be used alone or two or more kinds may be used in combination.

Examples of the carrier include liquid carriers such as water, alcohols (methanol, ethanol, isopropanol, glycol, glycerol and the like), ketones (acetone, methylethyl ketone and the like), aliphatic hydrocarbons (hexane, liquid paraffin and the like), aromatic hydrocarbons (benzene, xylene and the like), halogenated hydrocarbon, acid amide, ester, nitrile and the like; solid carriers such as clays (kaolin, bentonite, acid clay and the like), talcs (talc powder, agalmatolite powder and the like), silicas (diatomaceous earth, silicic anhydride, mica powder and the like), alumina, sulfur powder, activated carbon and the like; and the like. These carriers may be used alone or two or more kinds may be used in combination.

The total content ratio of the aforementioned active ingredient in the agent of the present invention can be appropriately set according to the dosage form, use embodiment and the like. It is generally 1-100 mass % and, from the aspect of cost-effectiveness, preferably 5-100 mass %, more preferably 5-95 mass %.

When the agent of the present invention contains one of the 1,9-nonanedial and 2-methyl-1,8-octanedial as the active ingredient, the "total content ratio of the active ingredient" here is a content ratio thereof. When the agent of the present invention contains both 1,9-nonanedial and 2-methyl-1,8-octanedial as the active ingredient, it is the total content ratio thereof.

The production method of the agent of the present invention is not particularly limited, and a method known per se or a method analogous thereto can be used. For example, it can be produced by adding and mixing components conventionally used in the field of biocorrosion inhibitors to and with 1,9-nonanedial and/or 2-methyl-1,8-octanedial when desired, and the like.

Examples of the dosage form in the present invention include emulsion, liquid, water solvent, wettable powder, powder, particle, micro particle, tablet, paste, suspension, spray, embrocation and the like. A method for formulating into each dosage form is not particularly limited, and a method known per se or a method analogous thereto can be used for formulation.

1,9-Nonanedial and/or 2-methyl-1,8-octanedial as the active ingredient of the agent of the present invention show sterilizing action equivalent to or not less than that of glutaraldehyde on the microorganism causing the biocorrosion, high safety and superior preservation stability. Therefore, the agent of the present invention is preferably used for inhibiting biocorrosion of a metal. In the present invention, "biocorrosion" refers to a corrosion phenomenon directly or indirectly induced by the action of microorganisms in the environment. Examples of the microorganism causing the biocorrosion include, but are not limited to, sulfate-reducing bacterium, nitrate-reducing bacterium, methane-producing bacterium, iodide-oxidizing bacterium, iron-oxidizing bacterium, sulfur-oxidizing bacterium and the like. In the present invention, moreover, "inhibition" of biocorrosion is a concept including prevention of the development of biocorrosion, and inhibition of the progress (exacerbation) of biocorrosion.

In the present invention, the "sulfate-reducing bacterium" is a generic term for microorganisms having an ability to reduce sulfate. Specific examples of sulfate-reducing bacterium include microorganism belonging to the genus *Desulfovibrio*, microorganism belonging to the genus *Desulfobacter*, microorganism belonging to the genus *Desulfotomaculum* and the like.

In the present invention, the "nitrate-reducing bacterium" is a generic term for microorganisms having an ability to reduce nitrate salt.

In the present invention, the "methane-producing bacterium" is a generic term for microorganisms having an ability to produce methane under an anaerobic environment. Specific examples of the methane-producing bacterium include microorganism belonging to the genus *Methanobacterium*, microorganism belonging to the genus *Methanococcus*, microorganism belonging to the genus *Methanosarcina* and the like.

In the present invention, the "iodide-oxidizing bacterium" is a generic term for microorganisms having an ability to oxidize iodide ion ($I^-$) into molecular iodine ($I_2$). Specific examples of the iodide-oxidizing bacterium include *Roseovarius* sp.2S-5, iodide oxidizing bacterium MAT3 strain and the like.

In the present invention, the "iron-oxidizing bacterium" is a generic term for microorganisms having an ability to oxidize a divalent iron ion ($Fe^{2+}$) into a trivalent iron ion ($Fe^{3+}$). Specific examples of the iron-oxidizing bacterium include *Mariprofundus ferrooxydans*, *Acidithiobacillus ferrooxidans* and the like.

In the present invention, the "sulfur-oxidizing bacterium" is a generic term for microorganisms having an ability to oxidize sulfur or inorganic sulfur compound. Specific examples of the sulfur-oxidizing bacterium include bacterium belonging to the genus *Thiobacillus*, bacterium belonging to the genus *Acidithiobacillus*, archaeum belonging to the genus *Sulfolobus*, archaeum belonging to the genus *Acidianus* and the like.

The agent of the present invention is preferably used for inhibiting biocorrosion due to at least one kind selected from sulfate-reducing bacterium, nitrate-reducing bacterium, methane-producing bacterium, iodide-oxidizing bacterium, iron-oxidizing bacterium and sulfur-oxidizing bacterium (more preferably at least one kind selected from sulfate-reducing bacterium, nitrate-reducing bacterium and methane-producing bacterium, further preferably at least one kind selected from sulfate-reducing bacterium and methane-producing bacterium, particularly preferably methane-producing bacterium).

The methane-producing bacterium prefers an anaerobic environment, and lives in paddy field, and further in marsh, pond, lake, river, sea, fossil fuel mining site and the like.

The sulfate-reducing bacterium prefers an anaerobic environment, and lives in mostly any environment containing water, for example, forest soil, farm, marsh, pond, lake, river, sea and the like.

The nitrate-reducing bacterium prefers an anaerobic environment, can live even in an oxidative environment as compared to the methane-producing bacterium and sulfate-reducing bacterium, and therefore, lives in the above-mentioned environments.

The iron-oxidizing bacterium is present in mine wastewater and the like. It also lives in a place containing a small amount of brown deposits and the like in the river and the like, and the like.

The sulfur-oxidizing bacterium lives in an environment similar to that where the iron-oxidizing bacterium lives, and also lives in domestic wastewater. Accordingly, it is also involved in concrete corrosion and the like of sewer pipes. Furthermore, it also lives in hot springs containing sulfur.

The iodide-oxidizing bacterium is comparatively frequently present in underground salt water, and is also widely present in a marine environment.

Therefore, the agent of the present invention is preferably used for inhibiting biocorrosion of a metal present or installed in the aforementioned habitat environments of microorganisms.

The metal to which the agent of the present invention is applied is not particularly limited as long as it is exposed to an environment where a microorganism causing the biocorrosion is present, and examples thereof include iron, copper, zinc, tin, aluminum, magnesium, titanium, nickel, chrome, manganese, molybdenum, alloy containing at least one kind selected therefrom and the like. Of these, iron and alloy containing iron is preferable, and iron is more preferable, from the aspect of industrial utilization.

While the use method of the agent of the present invention is not particularly limited as long as the object of the present invention is not impaired, one embodiment thereof when, for example, a metal is exposed to an environment where a microorganism causing the biocorrosion is present is a method including placing the agent of the present invention in the environment in advance of the exposure and the like. A specific example of the embodiment include adding and dissolving the agent of the present invention to and in a liquid (high-pressure water) to be injected at a high-pressure against bed-rock and the like in mining of fossil fuels (e.g., petroleum, natural gas, shale oil, shale gas and the like) by hydraulic fracturing, whereby the development of biocorrosion of a metal (e.g., metal piping to be the flow path of high-pressure water and the like) to be in contact with the high-pressure water can be inhibited. Alternatively, when a metal is exposed to an environment where microorganism causing the biocorrosion is present, the agent the present invention may be placed in the environment during exposure of the metal. Another embodiment is, for example, a method including applying or spraying the agent of the present invention as it is or after dissolving or dispersing in water, organic solvent and the like to the surface of a metal in need of inhibition biocorrosion or the like.

The use form of the agent present invention is preferably an aqueous solution having a total concentration of the aforementioned active ingredient within a particular range.

The total concentration of the active ingredient in the aqueous solution is generally not more than 10000 ppm and, from the aspect of cost-effectiveness, preferably 1-3000 ppm, more preferably 10-1000 ppm. When the concentration is less than 1 ppm, the biocorrosion inhibitive effect tends to be small, and when it exceeds 10000 ppm, a large excess state makes use thereof difficult in terms of the cost. In the present specification "ppm" means "mass ppm" unless otherwise specified.

As used herein, the "total concentration of the active ingredient" is a concentration of one of 1,9-nonanedial and 2-methyl-1,8-octanedial when the aqueous solution contains same as the sole active ingredient, or a total concentration of 1,9-nonanedial and 2-methyl-1,8-octanedial when the aqueous solution contains the both as the active ingredient.

The production method of the aqueous solution is not particular limited, a method known per se or a method analogous thereto can be used. For example, it can be produced by adding the aforementioned active ingredient to a suitable liquid carrier, and stirring e mixture to dissolve or disperse same. Examples of the liquid carrier include the liquid carrier and the like exemplified above as one of the components that the agent of the present invention may contain.

The aqueous solution can be utilized as high-pressure water etc. to be used for, for example, hydraulic fracturing. When the aqueous solution is used as the high-pressure water, the aqueous solution may contain components (e.g., proppant, viscosity modifier, surfactant, acid and the like) conventionally used for high-pressure water.

The aqueous solution may also be applied or sprayed on the surface of a metal in need of inhibition of biocorrosion.

When the agent of the present invention is used, a sterilizing method known per se or a method analogous thereto may be used in combination, as long as the object of the present invention is not impaired.

For example, a known antibacterial agent may be used in combination, or a sterilizing method by pH control (e.g., WO 2010/056114, WO 2008/134778 and the like), a sterilizing method by insonation (see, for example, WO 2000/024679 and the like) and the like may be used in combination. Examples of known antibacterial agents that can be used in combination with the agent of the present invention include other antibacterial agents exemplified above as one of the components that may be contained in the agent of the present invention.

EXAMPLES

The present invention is explained in more detail in the following by referring to Examples, which are not to be construed as limitative.

Example 1

Production of Mixture of 1,9-nonanedial (NL) and 2-methyl-1,8-octanedial (MOL)

By the method described in JP-B-2857055, a mixture of 1,9-nonanedial (hereinafter to be referred to as NL) and 2-methyl-1,8-octanedial (hereinafter to be referred to as MOL) was produced. The mass ratio of NL and MOL in the mixture is NL/MOL=85/15.

[Preparation of Inorganic Salt Sea Water Medium (Solution A)]

Milli-Q water 970 ml, NaCl $MgCl_2.6H_2O$ 2.6 g, $CaCl_2.2H_2O$ 0.15 g, $Na_2SO_4$ 4.0 g, $NH_4Cl$ 0.25 g, $KH_2PO_4$ 4.0 g, KCl 0.5 g, HEPES (2-[4-(2-hydroxyethyl)-1-piperazinyl]ethanesulfonic acid) 23.8 g were mixed and dissolved in an anaerobic chamber to prepare an inorganic salt sea water medium (solution A).

Milli-Q water is ultrapure water produced using an apparatus manufactured by Merk Millipore (e.g., Milli-Q Integral 10).

[Preparation of Sodium Bicarbonate Solution (Solution C)]

$NaHCO_3$ (2.52 g) was dissolved in Milli-Q water (30 ml), and the mixture was sterilized by filtration to prepare a sodium bicarbonate solution (solution C).

[Preparation of Trace Element Solution (Solution E)]

HCl (35%) 8.3 ml, $FeSO_4.7H_2O$ 2100 mg, $H_3BO_4$ 30 mg, $MnCl_2.4H_2O$ 100 mg, $CoCl_2.6H_2O$ 190 mg, $NiCl_2.6H_2O$ 24 mg, $CuCl_2.2H_2O$ 2 mg, $ZnSO_4.7H_2O$ 144 mg and $Na_2MoO_4.2H_2O$ 36 mg were mixed and the mixture was scaled up to 100 ml with Milli-Q water and sterilized by filtration to prepare a trace element solution (solution E).

[Preparation of Selenium-Tungsten Solution (Solution S)]

NaOH 400 mg, $Na_2SeO_3$ 4 mg and $Na_2WO_4.2H_2O$ 8 mg were mixed and the mixture was scaled up to 100 ml with Milli-Q water and sterilized by filtration to prepare a selenium-tungsten solution (solution S).

[Preparation of Vitamin Solution (Solution V)]

4-Aminobenzoic acid 4 mg, D-biotin 1 mg, nicotinic acid 10 mg, calcium D-pantothenate 5 mg, pyridoxine hydrochloride 15 mg, thiamine hydrochloride 10 mg, and vitamin B12 5 mg were mixed, and the mixture was scaled up to 100 ml with Milli-Q water and sterilized by filtration to prepare a vitamin solution (solution V).

Solution A was subjected to gas substitution for about 10 min, heated in an autoclave at 121° C. for 20 min, solution C, solution E, solution S and solution V were added, and the obtained mixture was dispensed by 20 ml to a vial containing a sterilized iron foil (0.08 g iron foil (length 10 mm×width 10 mm×thickness 0.1 mm: Sigma-Aldrich356808-G)). Each vial was subjected to gas substitution for 5 min ($N_2$ gas was mixed with $CO_2$ gas to finally give 20% $CO_2$ gas), and the vial was quickly closed with a butyl rubber stopper and the stopper was certainly fixed with an aluminum seal. Using a syringe, *Methanococcus* maripaludis KA-1 strain (0.5 ml) ($10^6$-$10^9$ cells/ml) was added, and (1) mixture of NL and MOL (mass ratio: NL/MOL=75/25, or NL/MOL=92/8), and (2) glutaraldehyde were added at the concentration shown in FIG. 1 or FIG. 2. Each vial was stood at 37° C. for 14 days, and the elution concentration of iron was measured to confirm the degree of biocorrosion progress in the iron foil. The measurement of elution concentration of iron included taking the solution (1.0 ml) in each vial, adding 6 M HCl (0.5 ml) to dissolve insoluble iron, adding 1 M L-ascorbic acid (1.0 ml) to reduce trivalent iron to divalent iron, and colorimetric measurement thereof by the ortho-Phenanthroline method. The results are shown in, FIG. 1 (mixture of NL and MOL) and FIG. 2 (glutaraldehyde).

Figure 2:
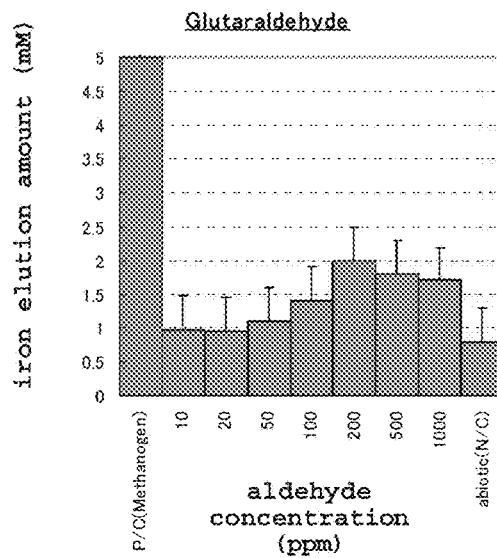
FIG. 2 shows a graph of the measurement results of iron elution concentration in a vial added with glutaraldehyde in Example 1. The abbreviations in the Figure mean the following.
abiotic (N/C): without addition of KA-1 strain and aldehydes
P/C (Methanogen): KA-1 strain is added but aldehydes are not added

As is clear from the results of FIG. 1 and FIG. 2, the elution concentration of iron in the vial added with a mixture of NL and MOL was of the same level as or not more than that with the addition of glutaraldehyde. Therefore, NL and MOL were shown to have a good biocorrosion inhibitive action or a biocorrosion inhibitive action comparable to that of glutaraldehyde.

Example 2

Measurement of oral toxicity, toxicity test on algae, bactericidal test on sludge, and biodegradability test were performed for NL, MOL and glutaraldehyde. The test methods and the results are as shown below.

<Oral Toxicity Test>

A test substance was emulsified and dispersed in 2%-gum arabic aqueous solution (containing 0.5%-Tween80), and forcibly administered to 6-week-old male CRj:CD(SD) rats with an oral gavage needle once per day for 14 days. The body weight variation and general condition were observed during the dosing period. The rats were fasted for one day from the final administration day (with free ingestion of drinking water), and anatomy, collection of blood samples (various blood tests), and mass measurement of the major organs were performed the next day of the final administration. In addition, histopathological examination (optical microscopic observation of HE-stained sliced section) of the liver, kidney, spleen and testis was also performed. The dose was 1000, 250, 60, 15 or 0 mg/k day (administered liquid amount=1 ml/100 g (body weight)/day), and 5 rats were used for each dose.

Test Substances:
(1) NL (GC purity: 99.7%)
(2) Glutaraldehyde (water content 101 ppm, GC purity: 99.8%)

As a result of the test, death case was not found with NL even at the maximum dose of 1000 mg/kg/day. NL does not fall under a "deleterious substance". The No Observed Effect Level (NOEL) under the test conditions is shown in Table 1.

TABLE 1

Table 1. Oral toxicity test results

| test substance | NOEL |
|---|---|
| NL | 250 mg/kg |
| glutaraldehyde | 5 mg/kg |

<Toxicity Test on Algae>

By reference to the OECD test guideline No. 201, an algae growth inhibitory test of a test substance was performed. To be specific, the following test substance was diluted with a test medium to give a defined dose. A suspension of algae grown to the exponential growth phase by preculture was added at an initial concentration of $1×10^4$ cells/ml. After shaking culture in a light irradiation-type bio shaker (Bio Shaker BR-180 LF manufactured by TAITEC) at 23° C., algae cells were counted by a flow cytometer (Cell Lab Quant SC manufactured by BECKMAN COULTER) at 24, 48, and 72 hr from the start of the test, and the growth degree of each test dose was calculated based on the growth degree of the normal control as 100%. Also, $ErC_{50}$ was calculated from the equation of the approximate curve in a graph plotting the growth inhibitory rate. As a standard substance, potassium dichromate was used.

algae: *Pseudokirchneriella subcapitata*

Test Substances:

(1) mixture of NL and MOL (GC purity: 98.7%, NL/MOL=59/41)

(2) glutaraldehyde (water content 101 ppm, GC purity: 99.8%)

Dose of Test Substance:

test substance (1) and test substance (2), 100, 32, 10, 3.2, 1, 0.32 mg/L (geometric ratio: $\sqrt{10}$) and 0 mg/L (normal control), respectively standard substance: 3.2, 1, 0.32 mg/L and 0 mg/L (normal control)

In this test, $ErC_{50}$ of potassium dichromate (standard substance) at 72 hr later was 1.3 mg/L, the growth ratio of normal control at 72 hr later was 93.0%, from which this test was assumed to have proceeded normally. The test results are shown in Table 2.

TABLE 2

Table 2. Toxicity test results on algae

| test substance | $ErC_{50}$ (72 hr) |
|---|---|
| NL/MOL (mass ratio 59/41) | 28.2 mg/L |
| glutaraldehyde | 9.0 mg/L |

<Bactericidal Test on Sludge>

Glucose, peptone, and monopotassium dihydrogen phosphate (each 5 g) were dissolved in water (1 L), and adjusted to pH 7.0±1.0 with sodium hydroxide to give synthetic sewer water, to which sludge in the sewage treatment plant in Mizushima area, Kurashiki-shi, Okayama-ken, Japan, was added at 30 ppm based on dry mass, whereby a bacterial culture was prepared. On the other hand, a test substance was diluted with distilled water in 10 phases to a final concentration of 1000-0.004 ppm (geometric ratio=4) on a 24 well microplate, and used as a test solution. Two wells were used for each concentration. As a comparison target, distilled water+bacterial culture was used as "bacterial culture blank", and distilled water alone was used as "blank".

The bacterial culture and test solution prepared above were mixed at a volume ratio 1:1, stood in a thermostatic tank at ambient temperature (about 25° C.) for 24 hr and 48 hr, and the level of sludge influence at each concentration of the test substance was visually observed and confirm by the MTT method. MTT reagent is converted by microorganism mitochondria in the sludge, forms formazan and develops a blue color. When the microorganism dies, this reaction does not occur and the reagent shows yellow.

Test Substances:

(1) mixture of NL and MOL (GC purity: 98.7%, NL/MOL=59/41)

(2) glutaraldehyde (water content 101 ppm, GC purity: 99.8%)

The results are shown in Table 3.

TABLE 3

Table 3. Bactericidal test results on sludge

| test substance | sterilizing concentration |
|---|---|
| NL/MOL (mass ratio 59/41) | 250 ppm |
| glutaraldehyde | 63 ppm |

<Biodegradability Test>

By reference to the test methods of the OECD test guideline 301C, JIS K 6950 (ISO 14851), a decomposition degree test of the test substance was performed. That is, an inorganic medium solution (300 ml) and activated sludge 9 mg (30 ppm) obtained on the day of the start of the test from the sewage treatment plant in Mizushima area, Kurashiki-shi, Okayama-ken, Japan, were placed in a culture bottle. Since the test substance has a sterilizing action, an influence on the sludge was considered, and a biodegradability test was performed at two concentrations of a high concentration group: test substance 30 mg (100 ppm), and a low concentration group: 9 mg (30 ppm).

Test Substances:

(1) mixture of NL and MOL (GC purity: 98.7%, NL/MOL=59/41)

(2) glutaraldehyde (water content 101 ppm, GC purity: 99.8%)

After culture using coulometer (Ohkura Electric Co., Ltd. 3001A type) at 25° C. for 28 days, the biodegradation ratio was calculated from the amount of oxygen consumed for the decomposition of the test substance and the theoretical oxygen demand determined from the structural formula of the test substance. As the biodegradable standard substance, aniline 30 mg (200 ppm) was used. When the biodegradation ratio was not less than 60%, the substance was judged to be a good degradable substance. The evaluation number of the test substance was n=2.

As a result of the measurement under the above conditions, aniline as a biodegradable standard substance showed a biodegradation ratio of not less than 60% during the test period, and was judged to have good degradability. Therefrom it was assumed that this test system was operated normally.

The biodegradation ratio of the NL/MOL high concentration group (100 ppm) at 28 days was 88.4%, 86.8% (average: 87.6%), and the group was judged to have "good degradability".

The biodegradation ratio of the NL/MOL low concentration group (30 ppm) at 28 days was 100.3%, 97.3% (average: 98.8%) and the group was judged to have "good degradability".

The biodegradation ratio of the glutaraldehyde high concentration group (100 ppm) at 28 days was 52.7%, 52.5% (average: 52.6%), and the group was judged to have "partial degradability (hardly degradable)".

The biodegradation ratio of the glutaraldehyde low concentration group (30 ppm) at 28 days was 78.5%, 77.5% (average: 78.0%), and the group was judged to have "good degradability".

From the above results, NL and/or MOL have/has low oral toxicity as compared to glutaraldehyde, the results of the toxicity test on algae are good, and the biodegradability is high.

Therefore, NL and/or MOL were/was shown to have high environmental and occupational safety as compared to glutaraldehyde.

Example 3

<Thermal Stability Test>

The following test solutions were each placed in a vial container, the airspace part was substituted with nitrogen, and tightly sealed and stored at 60° C. The NL/MOL or glutaraldehyde content of each test solution immediately after the start of storage was taken as 100%, and changes in the content 5 days later, 12 days later and 21 days later were observed according to the analytical curve method by gas chromatography using the internal standard. The results are shown in Table 4.

test solution 1: mixture of NL and MOL (mass ratio: 92/8)
test solution 2: mixture of NL/MOL/water=91:7:2 (mass ratio)
test solution 3: 50% glutaraldehyde aqueous solution (manufactured by Tokyo Chemical Industry Co., Ltd.)

[Gas Chromatography Analysis Conditions]

analysis instrument: GC-14A (manufactured by Shimadzu Corporation)
detector: FID (flame ionization detector)
column used: G-300 (length 20 m, film thickness 2 μm, inner diameter 1.2 mm)
(manufactured by Chemicals Evaluation and Research Institute)
analysis conditions: Inject. Temp. 250° C., Detect. Temp. 250° C.
temperature rise conditions: 80° C.→(temperature rise at 5° C./min)→230° C.
internal standard substance: diglyme (diethylene glycol dimethyl ether)

TABLE 4

Table 4. Thermal stability test results

|                | day 0 | 5 days later | 12 days later | 21 days later |
|----------------|-------|--------------|---------------|---------------|
| test solution 1 | 100%  | 100%         | 99%           | 98%           |
| test solution 2 | 100%  | 99%          | 98%           | 98%           |
| test solution 3 | 100%  | 96%          | 74%           | 62%           |

* calculated based on content at day 0 as 100%

In test solution 1 and test solution 2 containing NL and MOL, 98% remained even 21 days later; in test solution 3 containing glutaraldehyde, 62% remained 21 days later. Therefore, NL and/or MOL were/was shown to have high thermal stability than the glutaraldehyde aqueous solution.

INDUSTRIAL APPLICABILITY

Since the agent of the present invention contains 1,9-nonanedial and/or 2-methyl-1,8-octanedial as an active ingredient, it is superior in a metal biocorrosion inhibitive ability, and shows high environmental and occupational safety. The active ingredient of the agent of the present invention is also superior in the preservation stability.

Therefore, the agent of the present invention can be used for the inhibition of biocorrosion of high-pressure water or metal fluid to be used for, for example, hydraulic fracturing. In addition, the agent of the present invention can be used by applying or spraying on the surface of a metal in need of inhibition of biocorrosion.

Furthermore, the agent of the present invention can be effectively used for inhibiting biocorrosion of a metal present or installed in the habitat environments of microorganisms causing the biocorrosion.

This application is based on patent application No. 2013-237166 filed in Japan (filing date: Nov. 15, 2013), the contents of which are encompassed in full herein.

The invention claimed is:

1. A method of inhibiting biocorrosion of a metal, comprising placing an agent comprising 1,9-nonanedial and/or 2-methyl-1,8-octanedial as an active ingredient in an environment where a microorganism causing the biocorrosion is present,
   wherein said biocorrosion is caused by at least one kind selected from the group consisting of a sulfate-reducing bacterium, a nitrate-reducing bacterium, a methane-producing bacterium, an iodide-oxidizing bacterium, an iron-oxidizing bacterium and a sulfur-oxidizing bacterium.

2. A method of inhibiting biocorrosion of a metal, comprising sterilizing a microorganism causing the biocorrosion with an agent comprising 1,9-nonanedial and/or 2-methyl-1,8-octanedial as an active ingredient,
   wherein said biocorrosion is caused by at least one kind selected from the group consisting of a sulfate-reducing bacterium, a nitrate-reducing bacterium, a methane-producing bacterium, an iodide-oxidizing bacterium, an iron-oxidizing bacterium and a sulfur-oxidizing bacterium.

3. The method according to claim 1, wherein said metal is iron.

4. The method according to claim 2, wherein said metal is iron.

\* \* \* \* \*